United States Patent

Schroeder et al.

[11] 4,071,466
[45] Jan. 31, 1978

[54] OPTICAL BRIGHTENERS

[75] Inventors: Josef Schroeder, Cologne; Carl-Wolfgang Schellhammer, Schildgen, both of Germany

[73] Assignee: Bayer Aktiengesellschaft, Leverkusen, Germany

[21] Appl. No.: 648,658

[22] Filed: Jan. 13, 1976

Related U.S. Application Data

[62] Division of Ser. No. 447,211, March 1, 1974, abandoned.

Foreign Application Priority Data

[30]
Mar. 2, 1973   Germany .............................. 2310446
Mar. 2, 1973   Germany .............................. 2352245

[51] Int. Cl.² .................................................. D06L 3/12
[52] U.S. Cl. .......................... 252/301.22; 252/301.27; 8/1 W; 427/158; 260/239.9; 548/373
[58] Field of Search ................ 252/301.22, 301.27; 8/1 W; 427/158; 260/239.9, 310 D

[56] References Cited

U.S. PATENT DOCUMENTS 3,378,389   4/1968   Schellhammer et al. ... 260/310 D X
3,957,815   5/1976   Mengler ........................ 260/310 D Primary Examiner—John H. Mack
Assistant Examiner—Aaron Weisstuch
Attorney, Agent, or Firm—Plumley and Tyner

[57] ABSTRACT

Pyrazoline compounds of the formula

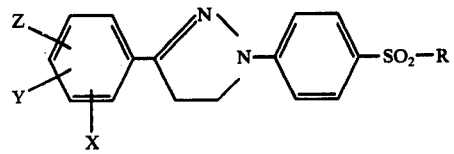

wherein R represents $C_3$-$C_{20}$-alkyl and X, Y and Z independently of one another represent hydrogen, halogen, $C_1$-$C_4$-alkyl, trifluoromethyl, $C_1$-$C_4$-alkoxy, aryl or acylamino, are useful as optical brighteners for macromolecular materials.

2 Claims, No Drawings

OPTICAL BRIGHTENERS

This is a division of application, Ser. No. 447,211, filed Mar. 1, 1974, abandoned.

The invention relates to compounds of the formula I

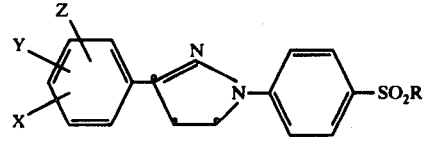

wherein
R represents $C_3$-$C_{20}$-alkyl, preferably $C_4$-$C_6$-alkyl, and especially $C_4$-alkyl and
X, Y and Z can be, independently of one another, H, halogen, such as chlorine and bromine or fluorine, $C_1$-$C_4$-alkyl, $CF_3$, $C_1$-$C_4$-alkoxy, aryl, especially phenyl, or acylamino, especially $C_2$-$C_5$-alkylcarbonylamino or benzoylamino, their preparation and use as optical brighteners for macromolecular materials, such as polyamides, polyolefines, polyacrylonitrile and cellulose esters, especially as brighteners for cellulose acetates which are incorporated during spinning.

The brighteners of the formula I particularly suitable for use as brighteners for incorporation into cellulose acetates by spinning when used as a mixture with pyrazolines of the formula II

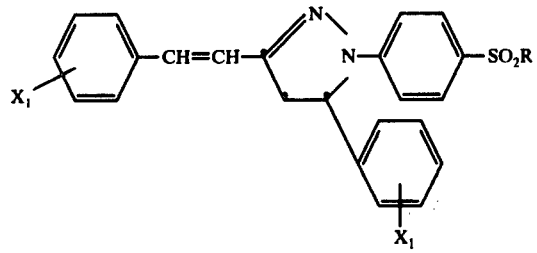

wherein
R has the abovementioned meaning and
$X_1$ represents H, $C_1$-$C_4$-alkyl, halogen such as chlorine and bromine, and $C_1$-$C_4$-alkoxy.

The mixing ratio of the pyrazolines I and II can be varied between 95:5 and 10:90 without significant change in the fastness properties and brightening properties.

The advantage of the mixture is that the shade of the resulting brightener can be varied as required.

Brighteners of the formula I, either by themselves or mixed with brighteners of the formula II,
wherein
Y and Z denote hydrogen,
X denotes chlorine,
$X_1$ denotes hydrogen and
R denotes n-butyl
are particularly preferred.

The pyrazolines I can be prepared in the usual manner by reaction of phenylhydrazines of the formula III

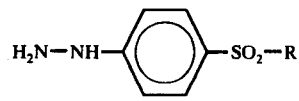

in which
R has the abovementioned meaning with vinyl ketones of the formula IV

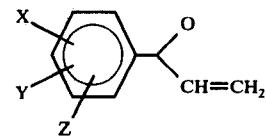

in which
X, Y and Z have the abovementioned meaning or with compounds which are precursors of the vinyl ketones, for example the corresponding Mannich bases or β-chloroketones. For preparing the pyrazolines II, the dibenzalacetones of the formula V

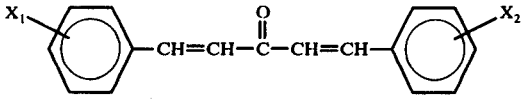

in which
$X_1$ has the abovementioned meaning
are reacted with the hydrazines of the formula III. The dibenzalacetones are readily obtainable according to known processes by condensation of acetone with benzaldehydes, using basic catalysts.

The pyrazolines of the formula I, by themselves or mixed with pyrazolines of the formula II, are suitable for brightening synthetic macromolecular substances such as polyamides, polyacrylonitrile, polyolefines and cellulose esters. They are particularly suitable for the brightening of cellulose esters by incorporation during spinning, because of their excellent solubility in solvents which are customary for the preparation of cellulose esters, for example acetone or methylene chloride/methanol. The procedure is to dissolve, for example, 1-p-butylsulphonyl-3-p-chlorophenyl-pyrazoline by itself or together with 1-p-butylsulphonyl-3-styryl-5-phenyl-pyrazoline in the ratio of 95:5 to 10:90, preferably 30:20 to 50:50, in a mixture of methylene chloride and methanol, 9:1 (100–200 g/l) and to add this solution to cellulose acetate spinning solutions in such amounts that the amount of brightener corresponds to 0.005–0.1% of the amount of cellulose acetate. Very good brightening of a reddish-tinged to neutral shade is thus achieved, depending on the amount of the 3-styrylpyrazoline added.

EXAMPLE 1

0.5 g of a solution of 100 g of 1[p(n-butylsulphonyl)phenyl]-3-[p-chlorophenyl]-Δ2-pyrazoline in 810 g of methylene chloride/90 g of methanol is added to a solution of 100 g of cellulose triacetate in approx. 810 g of methylene chloride and 90 g of methanol. Transparent films and sheets prepared therefrom are noticeably whiter than films and sheets produced without brightener. The brightening has a reddish-tinged shade.

The pyrazoline is prepared in the following manner:

255 g of p-butylsulphonylacetanilide, in a mixture of 1.5 l of water and 300 ml of concentrated hydrochloric acid, are boiled for 1 hour under reflux. After cooling to 0° C, the product is diazotised with a solution of 70 g of $NaNO_2$ in 175 ml of water. The filtered diazonium salt solution is added, at 5°–10° C, to a mixture of 750 g of 40% strength sodium sulphite solution and 750 ml of water which had been adjusted to pH 7 with concentrated sodium hydroxide solution, the pH being maintained at 6–7 by means of concentrated sodium hydroxide solution. After standing overnight, 300 ml of concentrated hydrochloric acid are added and the mixture is boiled for 1 hour. p-Butylsulphonylphenylhydrazine of melting point 138° C (from ethanol) is obtained, in a yield of approx. 70–75% of theory, from the cooled solution by careful addition of alkali.

22.8 g of the hydrazine in 100 ml of ethanol are heated to the boil with 5 ml of glacial acetic acid and 22.3 g of p,β-dichloropropiophenone are added. The pyrazoline gradually precipitates during the course of the reaction. After cooling, it is filtered off and washed with a little ethanol. 29–30 g of 1[p-(n-butylsulphonyl)-phenyl]-3-[p-chlorophenyl]-Δ2-pyrazoline are obtained.

The following pyrazolines are prepared similarly:

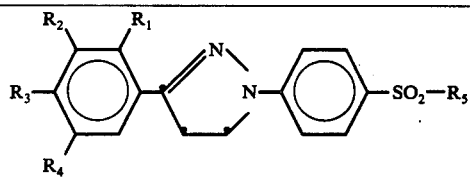

| $R_1$ | $R_2$ | $R_3$ | $R_4$ | $R_5$ |
|---|---|---|---|---|
| H | H | Cl | H | $C_3H_7$ |
| H | H | Cl | H | $C_5H_{11}$ |
| H | H | Cl | H | $C_{12}H_{25}$ |
| H | H | Cl | H | Allyl |
| H | H | Cl | H | Propenyl |
| $CH_3$ | H | Cl | Cl | $C_4H_9$ |
| $CH_3$ | H | Cl | $CH_3$ | $C_4H_9$ |
| Cl | H | Cl | H | $C_4H_9$ |
| Cl | H | Cl | Cl | $C_4H_9$ |
| Cl | H | H | H | $C_4H_9$ |
| H | H | Cl | Cl | $C_4H_9$ |
| $CH_3$ | H | Cl | H | $C_4H_9$ |
| $CH_3$ | H | Cl | Cl | $C_6H_{13}$ |
| F | H | H | H | $C_4H_9$ |
| $CF_3$ | H | H | H | $C_4H_9$ |
| H | H | $CH_3$ | $CH_3$ | $C_4H_9$ |
| H | Cl | H | H | $C_4H_9$ |
| H | $CH_3$ | Cl | H | $C_4H_9$ |

EXAMPLE 2

6 ml of a solution of 15 g of the pyrazoline described above in 1 l of acetone are added to a solution of 200 g of cellulose 2½-acetate in 800 g of acetone. The cellulose acetate filaments spun from this solution show very good brightening and good fastness to washing, light and water.

EXAMPLE 3

Polyacrylonitrile fabric is introduced, using a liquor ratio of 1:40, into an aqueous bath at 20° C which contains, per liter, 0.0075 to 0.075 of the brightener described in Example 1. The bath is slowly heated to 50°–60° C and is kept at this temperature for 20–40 minutes, whilst agitating the goods to be dyed gently in the bath. The fabric is then rinsed and dried and shows a brilliant reddish-tinged brightening.

EXAMPLE 4

0.5 g of a solution of 70 g of 1[p-butylsulphonylphenyl]-3-[p-chlorophenyl]Δ2-parazoline and 30 g of 1[p-butylsulphonylphenyl]-3-styryl-5-phenyl-Δ2-pyrazoline in 810 g of methylene chloride/90 g of methanol is added to a solution of 100 g of cellulose triacetate in approx. 810 g of methylene chloride and 90 g of methanol. Films and sheets produced therefrom show an outstanding brightening of a neutral shade.

1-[p-Butylsulphonylphenyl]-3-styryl-5-phenyl-Δ2-pyrazoline is prepared as follows:

86 g of dibenzalacetone and 99 g of p-butylsulphonylphenylhydrazine (84.6% strength) in 1 l of ethanol, in the presence of 30 ml of concentrated HCl, are stirred for 4 hours under reflux. Initially, the entire mixture dissolves at the boiling point. After refluxing for 1 hour, product begins to precipitate. After cooling, the product is filtered off, washed with a little ethanol, dried and recrystallised from glycol monomethyl ether; yield 110 g.

Further pyrazolines were prepared similarly:

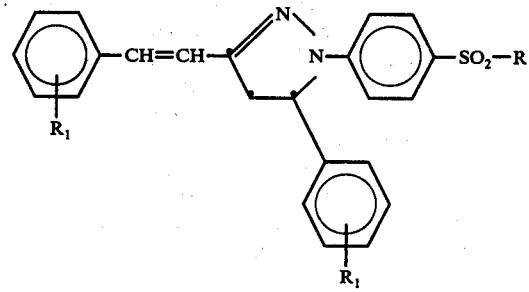

| R | $R_1$ | (Position) |
|---|---|---|
| $C_4H_9$ | Cl | 4 |
| $C_4H_9$ | $CH_3$ | 4 |
| $C_4H_9$ | $OCH_3$ | 4 |
| $C_4H_9$ | $CH_3$ | 2 |

We claim:

1. Process for brightening of synthetic macromolecular substances by treating said substances with a mixture of 95–10 percent by weight of a compound of the formula

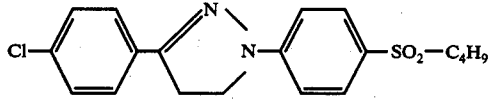

with the remaining 5–90 percent by weight of a compound of the formula

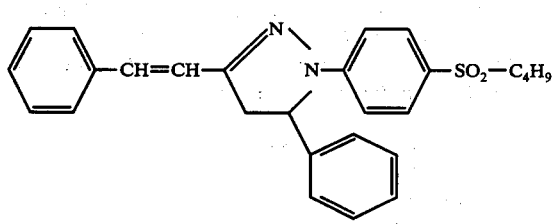

2. Process of claim 1 wherein said macromolecular substance is a cellulose ester spinning composition.

* * * * *